(12) United States Patent
Itahashi et al.

(10) Patent No.: US 7,553,988 B2
(45) Date of Patent: *Jun. 30, 2009

(54) METHOD FOR PRODUCING COUPLING COMPOUND

(75) Inventors: Tamon Itahashi, Osaka (JP); Takashi Kamikawa, Nara (JP)

(73) Assignee: Sumitomo Chemical Company, Limted, Osaka (JP)

( * ) Notice: Subject to any disclaimer, the term of this patent is extended or adjusted under 35 U.S.C. 154(b) by 324 days.

This patent is subject to a terminal disclaimer.

(21) Appl. No.: 11/465,167

(22) Filed: Aug. 17, 2006

(65) Prior Publication Data

US 2006/0281925 A1 Dec. 14, 2006

Related U.S. Application Data

(62) Division of application No. 10/757,148, filed on Jan. 14, 2004, now Pat. No. 7,217,677.

(30) Foreign Application Priority Data

Jan. 17, 2003 (JP) ............................. 2003-009637
Apr. 16, 2003 (JP) ............................. 2003-111282

(51) Int. Cl.
*C07C 69/00* (2006.01)

(52) U.S. Cl. .................. 560/130; 568/312; 568/322; 568/323; 568/626; 548/312.4; 502/167

(58) Field of Classification Search ............ 560/130; 568/312, 322, 323, 626; 548/312.4; 502/167
See application file for complete search history.

(56) References Cited

U.S. PATENT DOCUMENTS

| 5,922,898 | A | 7/1999 | Miller et al. |
| 6,194,599 | B1 | 2/2001 | Miller et al. |
| 6,395,916 | B1 | 5/2002 | Buchwald et al. |
| 7,041,856 | B2 | 5/2006 | Itahashi et al. |
| 7,238,832 | B2 * | 7/2007 | Itahashi et al. ............ 560/130 |
| 2002/0016489 | A1 | 2/2002 | Marcuccio et al. |
| 2003/0158419 | A1 | 8/2003 | Kamikawa et al. |
| 2003/0162950 | A1 | 8/2003 | Itahashi et al. |

FOREIGN PATENT DOCUMENTS

DE 152 547 12/1981

| EP | 0 366 573 A1 | 5/1990 |
| WO | WO 00/68252 A1 | 11/2000 |
| WO | WO 01/66248 A2 | 9/2001 |

OTHER PUBLICATIONS

Netherton et al., "Suzuki Cross-Coupling of Alkyl Tosylates that Possess β Hydrogen Atoms: Synthetic and Mechanistic Studies", *Angew. Chem. Int. Ed.*, vol. 41 No. 20, pp. 3910-3912, (2002).
Leadbeater et al., "Suzuki Aryl Couplings Mediated By Phosphine-Free Nickel Complexes", *Tetrahedron*, vol. 55, pp. 11889-11894, (1999).
Elgafi et al., "Synthesis of novel ruthenium complexes containing bidentate imidazole-based ligands", *J. Chem Soc. Dalton Trans.*, pp. 2341-2345, (1997).
Satake, "Synthesis of Neutral π-Allylpalladium Complexes having Bisnitrogen Ligands and Palladium-Catalyzed Cyclopropanation of Ketene Silyl Acetates with Allylic Acetals", *Journal of Synthetic Organic Chemistry*, vol. 58, No. 8, pp. 736-744, (2000).
Katalin OSZ[3], "Copper(II), nickel(II) and zinc(II) complexes of amino acids containing bis(imidazol-2-yl)methyl residues", *Inorganica Chimica Acta*, vol. 339, pp. 373-382, (2002).
Kirichhoff et al., "Boronic Acids: New Coupling Partners in Room-Temperature Suzuki Reactions of Alkyl Bromides. Crystallographic Characterization Of An Oxidative-Addition Adduct Generated under Remarkably Mild Conditions", *Journal of American Chemical Society*, vol. 124, No. 46, pp. 13662-13663, (2002).
Duñach et al., "Carbon-Carbon Bond Formation with Electrogenerated Nickel and Palladium Complexes", *European Journal of Organic Chemistry*, No. 9, pp. 1605-1622, (2003).

\* cited by examiner

*Primary Examiner*—Rei-tsang Shiao
(74) *Attorney, Agent, or Firm*—Panitch Schwarze Belisario & Nadel LLP

(57) ABSTRACT

A method is provided for producing a specific crosscoupling compound and a specific catalyst for producing the compound. The method includes reacting in the presence of a base and a nickel compound catalyst organic halide of the formula $n'(R^1X^1{}_n)$, wherein $R^1$ is a hydrocarbon group and the α and β carbons to X' are $sp^3$ carbon atoms; $X^1$ is a chlorine, bromine, or iodine atoms, and n and $n^1$ are 1 or 2 but not both 2, with a compound having the formula $m\{R^2(BX^2{}_2)_{n'}\}$ where an $R^2$ is an aryl, heteroaryl, or alkenyl group, and n' is 1 or 2, $X_2$ is independently a hydroxyl group, an alkoxy or arylalkoxy group or $X^2{}_2$ together form an alkylenedioxy or arylenedioxy group, and m represents 1 or 2 but m≦n, and the boron atom is bonded to a $sp^2$ carbon atom of $R^2$ group or a boronic acid trimer anhydride.

12 Claims, No Drawings

METHOD FOR PRODUCING COUPLING COMPOUND

CROSS-REFERENCE TO RELATED APPLICATIONS

This is a division of co-pending application Ser. No. 10/757,148, filed Jan. 14, 2004, the disclosure of which is incorporated herein by reference.

BACKGROUND OF THE INVENTION

The invention relates to a method for producing a coupling compound and to a cross-coupling catalyst. Coupling compounds are useful as pharmaceuticals, agricultural chemicals, liquid crystal materials, organic EL materials, or synthetic intermediates thereof.

There are disclosed Suzuki cross-coupling reactions between aryl halide compounds and aryl boron compounds catalyzed by palladium phosphine complexes and also a coupling reaction between aryl halide compounds and aryl boron compounds catalyzed by nickel phosphine compounds or a nickel catalyst containing nickel compounds and triethylamine or bipyridyl (e.g. Tetrahedron 55(1999) 11889-11894).

It is also disclosed (for example, Angew. Chem. Int. Ed., pp. 3910-3912, 2002) that cross-coupling of alkyl halides can be only achieved by using the expensive palladium phosphine complex compound but they are less reactive than aryl halides.

BRIEF SUMMARY

According to the present invention, a halide compound in which carbon atoms at the α and β positions relative to $X^1$ are $sp^3$ carbon atoms can be effectively used in a coupling reaction with an organic boron compound of which boron atom is bonded with a $sp^2$ carbon atom thereof in the presence of a nickel catalyst of the invention.

Thus, the present invention provides:
a method for producing a cross-coupling compound of formula (3):

$$(Y-)_{(n-1)}R^1-R^2-(R^1)_{(n'-1)} \qquad (3)$$

wherein $R^1$ represents
a substituted or unsubstituted, linear, branched, or cyclic hydrocarbon group, and
n and n' each represent 1 or 2,
provided that when n and n' are the same, both n and n' are not 2,
$R^2$ represents a substituted or unsubstituted aryl, heteroaryl or alkenyl group, and
Y represents $R^2$ or $X^1$, wherein $R^2$ is as defined above, and $X^1$ represents a chlorine, bromine or iodine atom,
which method comprises reacting
an organic halide of formula (1):

wherein $R^1$ is as defined above and carbon atoms at the α and β positions relative to $X^1$ are $sp^3$ carbon atoms, and $X^1$, n and n' are as defined above,
with a boron compound of formula (2):

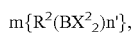

wherein $R^2$ and n' are as defined above, $X^2$ independently represents a hydroxyl group or an alkoxy or aryloxy group, or $X^2_2$ together form an alkylendioxy or arylenedioxy group, and m represents 1 or 2, and m≦n, and the boron atom is bonded with a $sp^2$ carbon atom of $R^2$ group, or a boronic acid trimer anhydride thereof, in the presence of a base and a catalyst comprising a nickel compound and a compound of formula (i):

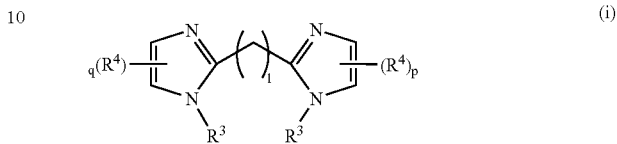

wherein $R^3$ represents a substituted or unsubstituted alkyl group,
$R^4$ represents a hydrogen atom or an substituted or unsubstituted alkyl group,
l represents an integer of 1 to 3, and
p and q each represents an integer of 0 to 2; and the catalyst.

DETAILED DESCRIPTION

A description is made to the embodiments of the present invention in detail below.

Examples of the nickel compound used in the inventive method include, for example, compounds of divalent or zero-valent nickel, and specifically a nickel salt, a complex salt of a divalent nickel compound, nickel hydroxide, a π complex compound of divalent or zero-valent nickel.

For example, the nickel salt is a salt of nickel and an inorganic or organic acid. Examples of the nickel salt of the inorganic acid include, for example, a nickel halide such as nickel(II) chloride, nickel(II) bromide and nickel(II) iodide, nickel(II) nitrate, nickel(II) sulfate, nickel(II) ammonium sulfate, and nickel(II) hypophosphite.

Examples of the nickel salt of the organic acid include, for example, for example, nickel(II) acetate, nickel(II) formate, nickel(II) stearate, nickel(II) cyclohexanebutyrate, nickel(II) citrate, and nickel(II) naphthenate.

Examples of the complex salt of the divalent nickel compound include, for example, an amine complex of divalent nickel such as nickel(II) hexaamine chloride or nickel(II) hexaamine iodide, and an acetylacetone complex salt of divalent nickel such as nickel acetylacetonate.

Examples of the nickel hydroxide include, for example, for example, nickel(II) hydroxide.

Examples of the π complex compound of divalent nickel include, for example, bis(η3-allyl)nickel(II), bis(η-cyclopentadienyl)nickel(II) and allynickel chloride dimer.

Examples of the π complex compound of zero-valent nickel include, for example, bis(1,5-cyclooctadiene)nickel (0) and nickelcarbonyl(0).

Such nickel compounds may be an anhydride or a hydrate.

Preferred nickel compound are nickel chloride, nickel bromide, nickel iodide, nickel nitrate, nickel acetate, and bis(1, 5-cyclooctadiene)nickel(0).

The nickel compound may be used in an amount of 0.00001 mole to 1 mole, preferably in a catalytically effective amount such 0.00001 mole to 0.2 mole, per mole of the halogen atom of the organic halide to be reacted.

The compound of formula (i) may be supported on a carrier such as a reaction solvent-insoluble resin so that the reaction can be carried out in a heterogeneous system.

The compound of formula (i) is used, for example, in an amount of about at least 0.1 mol, and preferably 1 to 10 moles, per mol of the nickel atom of the nickel compound. In the process of the present invention, the compound of formula (i) may be used in combination with any phosphine compound.

The catalyst may be prepared by contacting the nickel compound and the compound of formula (i) and isolating the resulting compound comprising the nickel compound and the compound of formula (i), which is typically coordinated thereto.

Alternatively, a catalyst preparation in a solution form, prepared by contacting the components in a suitable solvent, may be used in the coupling reaction as it is.

Alternatively, the nickel compound and the compound of formula (i) may each independently be added, as catalyst components, to the reactants of formula (1) and (2), typically in a suitable solvent.

A reducing agent may be reacted with the divalent nickel compound, as the catalyst component, or the catalyst comprising the nickel compound. Any reducing agent may be used without limitation, and preferred examples thereof include, for example, sodium borohydride, lithium aluminum hydride, sodium hydride, diisobutylaluminum hydride, an alkyl Grignard reagent, alkyl lithium, and zinc metal. For example, the catalyst may be typically prepared by adding the divalent nickel compound, the compound of formula (i) and the reducing agent, and optionally a suitable solvent, which is inert to the reducing agent, in an optional order. Examples of the solvent include, for example, those solvents that may be used in the coupling reaction as shown below, and an ether solvent or a hydrocarbon solvent is preferably used.

The nickel compound may be used, for example, in a completely dissolved form or suspended form in the reaction system containing the reactants and optionally a suitable solvent employed. The nickel compound may be used as it is or may be supported on a material such as carbon, silica or alumina that are insoluble to the reaction solvent and reactants.

The compound of formula (i) according to the invention is described in detail below.

Examples of the substituted or unsubstituted alkyl group represented by $R^3$ include, for example, an alkyl group having 1 to 4 carbon atoms such as methyl, ethyl, propyl, isopropyl, or butyl. Methyl is particularly preferred.

Examples of the substituted or unsubstituted alkyl group represented by R4 include, for example, an alkyl group having 1 to 4 carbon atoms such as methyl, ethyl, propyl, isopropyl, or butyl. The hydrogen atom is particularly preferred as $R^4$.

Specific examples of the compound of formula (i) include, for example, bis(N-methylimidazole-2-yl)methane, bis(1,2-(N-methylimidazole-2-yl))ethane, bis(1,3-(N-methylimidazole-2-yl))propane.

The integer represented by l is preferably 1.

Examples of the present coupling reaction include, for example, the following:

when n=n'=1, $R^1$—$X^1$+$R^2$-$(BX^2{}_2)$→$R^1$—$R^2$ (3a);

when n=2 and n'=1 (m=1), $X^1$—$R^1$—$X^1$+$R^2$-$(BX^2{}_2)$→$X^1$—$R^1$—$R^2$ (3b);

when n=2 and n'=1 (m=2), $X^1$—$R^1$—$X^1$+$2\{R^2$-$(BX^2{}_2)\}$→$R^2$—$R^1$—$R^2$ (3c); and when n=1 and n'=2, $2R^1$—$X^1$+$(BX^2{}_2)$-$R^2$-$(BX^2{}_2)$→$R^1$—$R^2$—$R^1$ (3d).

The organic halide in the embodiments of the present coupling reaction is described in detail below.

In the coupling reaction, $X^1$ is eliminated in the reaction with the boron compound, whereby a new carbon-carbon bond is formed between the carbon atoms, which were bonded with the boron atom and the halogen atom respectively. The sp³ carbon atom at α position relative to $X^1$ means an sp³ carbon atom bonded with the halogen atom, and the sp³ carbon atom at β position relative to $X^1$ is an sp³ carbon atom bonded with the sp³ α carbon atom. More preferably, the carbon atoms at α, β and γ positions relative to the halogen atom are sp³ carbon atoms.

$X^1$ preferably represents a bromine or iodine atom.

Examples of the substituted or unsubstituted, linear, branched or cyclic hydrocarbon group in which α and β carbon atoms relative to $X^1$ are sp³ carbon atoms, represented by $R^1$, include, for example, a linear, branched or cyclic $C_{2-30}$ alkyl group, and specific examples thereof include, for example, ethyl, propyl, isopropyl, butyl, pentyl, hexyl, heptyl, octyl, nonyl, decyl, undecyl, dodecyl, tridecyl, tetradecyl, octadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, triacontyl, cyclopentyl, cyclohexyl, and adamantly; and Examples of the substituted or unsubstituted, linear, branched or cyclic hydrocarbon group of which α and β carbon atoms relative to $X^1$ are sp³ carbon atoms, represented by $R^1$, include, for example, a linear, branched or cyclic $C_{4-30}$ alkenyl group, and specific examples thereof include, for example, butenyl, pentenyl, hexenyl, heptenyl, octenyl, nonenyl, decenyl, undecenyl, dodecenyl, tridecenyl, tetradecenyl, octadecenyl, hexadecenyl, heptadecenyl, octadecenyl, nonadecenyl, icosenyl, henicosenyl, docosenyl, tricosenyl, tetracosenyl, pentacosenyl, hexacosenyl, heptacosenyl, octacosenyl, nonacosenyl, triacontenyl, cyclopentenyl, and cyclohexeneyl.

Examples of the substituent of the substituted linear, branched or cyclic hydrocarbon group of which α and β carbon atoms relative to $X^1$ are sp³ carbon atoms include, for example, a fluorine atom, a hydroxyl group, an alkoxyl group such as ethoxy and tert-butoxy, an aryloxy group such as phenoxy group, a mercapto group, an alkylthio group such as methylthio, an arylthio group such as phenylthio, a cyano group, a nitro group, an amino group, an mono- or di-alkylamino group such as dimethylamino or cyclohexylamino, an alyl- or aryl-carbamate group such as tert-butylcarbamate, methylcarbamate, or phenylcarbamate, an aryl- or alkyl-sulfonamide group such as benzenesulfonamide or methanesulfonamide, an aryl- or alkyl-imino or imide group such as phthalimide, a formyl group, a carboxyl group, an alkoxycarbonyl group such as methoxycarbonyl, an aryloxycarbonyl group such as p-methoxyphenoxycarbonyl or phenoxycarbonyl, a carbamoyl, an N-alkyl- or N-aryl-carbamoyl such as N-phenylcarbamoyl, a heterocylic group such as pyridyl, quinazolinyl, pyrimidyl, furyl, thienyl, pyrrolyl, and imidazolyl, and an aryl group such as phenyl, or naphthyl. The term "alkyl" contained in the substituents in the preceding paragraph typically means $C_{1-8}$ alkyl group such as methyl, ethyl, propyl, butyl, pentyl, hexyl, heptyl, or octyl, and the term "aryl" contained in the substituents in the preceding paragraph typically means $C_{6-10}$ aryl group such as phenyl, naphthyl, tolyl, xylyl or anisyl.

Two substituents on adjacent carbon atoms of $R^1$ may be bonded to form a condensed ring together with $R^1$. Any of these substituents may also be substituted.

Examples of the organic halide include, for example, 1-chlorobutane, 1-chloropentane, 1-chlorohexane, 1-chloroheptane, 1-chlorooctane, 1-chlorononane, 1-chlorodecane, 1-chlorododecane, 1-chlorotridecane, chlorotetradecane, 1-chloropentadecane, 1-chlorohexadecane, 1-chlorooctadecane, 1-chloroeicosane, 1-chlorodocosane, 2-chloropropane, 1-bromo-2-methylpropane, 2-bromopentane, 3-bromopentane, (S)-(+)-1-bromo-2-methylbutane, 1-bromo-3-methylbutane, 1-bromo-2,2-dimethylpropane, 1-bromo-2-ethylethane, 2-bromoheptane, 2-ethylhexyl bromide, 2-bromodecane, 2-bromododecane, 2-bromotridecane, 1,2-dibromoethane, 1,3-dichloropropane, 1,4-dibromobutane, 1,5-dichloropentane, 1,6-dichlorohexane, 1,7-dichloroheptane, 1,8-dichlorooctane, 1,9-dichlorononane, 1,10-dichlorodecane, 1,11-dichloroundecane, 1,12-dichlorododecane, 2-bromo-1-chloropropane, 1-chloroheptadecafluorooctane, 4-chloro-1-butene, 5-chloro-1-pentene, 6-chloro-1-hexene, 8-chloro-1-octene, 3-chloro-propanol, 8-bromo-1-octanol, 9-chloro-1-nonanol, 10-chloro-1-decanol, 11-chloro-1-undecanol, 12-chloro-1-dodecanol, chloromethyl octyl ether, 1-bromopropane, 1-bromobutane, 1-bromopentane, 1-bromohexane, 1-bromoheptane, 1-bromooctane, 1-bromononane, 1-bromodecane, 1-bromododecane, 1-bromotridecane, bromotetradecane, 1-bromopentadecane, 1-bromohexadecane, 1-bromooctadecane, 1-bromoeicosane, 1-bromodocosane, 2-bromopropane, 1-bromo-2-methylpropane, 2-bromopentane, 3-bromopentane, (S)-(+)-1-bromo-2-methylbutane, 1-bromo-3-methylbutane, 1-bromo-2,2-dimethylpropane, 1-bromo-2-ethylethane, 2-bromoheptane, 2-ethylhexyl bromide, 2-bromodecane, 2-bromododecane, 2-bromotridecane, 1,2-dibromoethane, 1,3-dibromopropane, 1,4-dibromobutane, 1,5-dibromopentane, 1,6-dibromohexane, 1,7-dibromoheptane, 1,8-dibromooctane, 1,9-dibromononane, 1,10-dibromodecane, 1,11-dibromoundecane, 1,12-dibromododecane, 2-bromo-1-chloropropane, 1,2-dibromopropane, 1,2-dibromobutane, 1,3-dibromobutane, 2,3-dibromobutane, 1-bromo-3-chloro-2-methylpropane, 1,2-dibromo-2-methylpropane, 1,4-dibromopentane, 1,2-dibromo-3,3-dimethylbutane, 1-bromoheptadecafluorooctane, 4-bromo-1-butene, 5-bromo-1-pentene, 6-bromo-1-hexene, 5-bromo-2-methyl-2-pentene, 8-bromo-1-octene, (R)-(−)-citronellyl bromide, (R)-(+)-citronellyl bromide, cyclobutyl bromide, cyclohexyl bromide, cycloheptyl bromide, (bromomethyl)cyclohexane, 3-bromopropanol, (R)-3-bromo-2-methyl-1-propanol, 8-bromo-1-octanol, 9-bromo-1-nonanol, 10-bromo-1-decanol, 11-bromo-1-undecanol, 12-bromo-1-dodecanol, 1,4-dibromo-2-butanol, 1,3-dibromo-2-propanol, 2-bromoethyl methyl ether, 2-bromoethyl ethyl ether, 2-bromoethyl ether, bromomethyl octyl ether, 1-iodopropane, 1-iodobutane, 1-iodopentane, 1-iodohexane, 1-iodoheptane, 1-iodooctane, 1-iodononane, 1-iodododecane, 1-iodododecane, 1-iodotridecane, 1-iodotetradecaen, 1-iodopentadecane, 1-iodohexadecane, 2-iodopropane, 2-iodobutane, 1-iodo-2-methylpropane, (S)-(+)-1-iodo-2-methylbutane, 1-iodo-2,2-dimethylpropane, 1,2-diiodoethane, 1,3-diiodopropane, 1,4-diiodobutane, 1,5-diiodopentane, 1,6-diiodohexane, 1,8-diiodooctane, 1,10-diiododecane, perfluorobutyl iodide, 1-iodoheptadecafluorooctane, 1,1,1,2,2,3,3,4,4,5,5,6,6-tridecafluoro-8-iodooctane, 1,1,1,2,2,3,3,4,4,5,5,6,6,7,7,8,8-heptadecafluoro-10-iododecane, perfluorodecyl iodide, perfluorododecyl iodide, and cyclohexyl iodide.

In the boron compound of formula (2), examples of the substituted or unsubstituted aryl group represented by $R^2$ include, for example, any aryl group including those having one to four aryl rings, and preferably having 6 to 16 carbon atoms.

Examples of the unsubstituted aryl group include, for example, phenyl, naphthyl, anthracenyl, phenanthryl, indenyl, fluorenyl, and pyrenyl.

Examples of the unsubstituted heteroaryl group represented by $R^2$ include, for example, pyridyl, quinazolyl, quinolyl, pyrimidyl, furyl, thienyl, pyrrolyl, imidazolyl, and tetrazolyl.

In the organic halide compound of formula (2), when $R^2$ is an aLkenyl group, the boron atom is bonded with a sp$^2$ carbon atom of the alkenyl carbon-carbon double bond, which may also be conventionally referred to as a "vinyl carbon atom".

Examples of the alkenyl group represented by $R^2$ include, for example, vinyl, 1-propenyl and those shown as the examples of the alkenyl group represented by $R^1$ of the organic halide of formula (1).

Preferred alkenyl group are a substituted or unsubstituted $C_2$ to $C_{10}$ alkenyl group having one or more double bonds.

Examples of the substituted aryl, heteroaryl and alkenyl groups include, for example, the aryl, heteroaryl and alkenyl groups substituted with at least one group selected from those substituent groups as exemplified for the substituent group of the substituted linear, branched or cyclic hydrocarbon group represented by $R^1$.

Examples of the alkoxy group represented by $X^2$ include, for example, methoxy, ethoxy propoxy, butoxy, pentyloxy, hexyloxy, heptyloxy, or octyloxy. Alternatively two alkoxyl groups are bonded to form, for example, an alkylendioxy (e.g. dimethylenedioxy, trimethylenedioxy or pinacoloxy ) or arylenedioxy group (e.g. catecholoxy), and specific examples thereof include, boronic acid-pinacol ester or boronic acid-catechol ester. When $R^2$ groups form a residue of a boronic acid trimer anhydride, $X^2{}_2$ represent —O—B($R^2$)—O—B($R^2$)—O—.

When $R^2$ group represents the substituted aryl or heteroaryl group or represents an ortho-condensed, or ortho and peri-condensed polycyclic aromatic ring, one of the ortho positions of the $BX^2{}_2$ group preferably is unsubstituted.

A preferred boron compound of formula (2) wherein $R^2$ is an aryl group is a compound of formula (4):

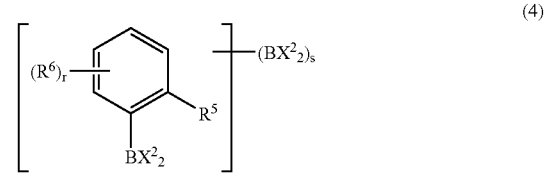

(4)

wherein $R^5$ represents a hydrogen atom, $X^2$ groups independently represent a hydroxy group or an alkoxy group, or the alkoxy groups together form an alkylenedioxy group (e.g. dimethylene, trimethylene or pinacol alcohol residue), or $X^2{}_2$ represent —O—B($R^{20}$)—O—B($R^{20}$)—O—, wherein $R^{20}$ represents the phenyl residue as defined in connection with formula (4) above, r represents an integer of 0 to 4, s represents 0 or 1, r+s≦4 when the benzene ring does not form a condensed aromatic ring, $R^6$ groups are the same or different and independently represent a substituted or unsubstituted aryl group, a substituted or unsubstituted heteroaryl group, or a substituted or unsubstituted linear, branched or cyclic alkenyl group, or $R^6$ groups on adjacent carbon atoms of the benzene ring are optionally bonded to form a condensed polycyclic aromatic ring, for example, in which the $R^6$ groups are ortho-condensed (e.g. naphthalene, anthracene, phenanthrene), or ortho and peri-condensed with the benzene ring (e.g. pyrene). Preferably, the ortho position of the $BX^2{}_2$ group is unsubstituted, that is, a hydrogen atom.

When $X^2$ is a hydroxy group, the boron compound of formula (2) may form an acid anhydride of formula (5) below.

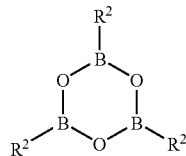

(5)

wherein $R^2$ is as defined in connection with formula (2).

Examples of the boron compound (2) include, for example, phenylboronic acid, 2-methylphenylboronic acid, 3-methylphenylboronic acid, 4-methylphenylboronic acid, 2,3-dimethylphenylboronic acid, 4-dimethylphenylboronic acid, 2,5-dimethylphenylboronic acid, 2-ethylphenylboronic acid, 4-n-propylphenylboronic acid, 4-isopropylphenylboronic acid, 4-n-butylphenylboronic acid, 4-tert-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9-fluorenylboronic acid, 9-phenanthrenylboronic acid, 9-anthracenylboronic acid, 1-pyrenylboronic acid, 2-trifluoromethylphenylboronic acid, 3-trifluoromethylphenylboronic acid, 4-trifluorophenylboronic acid, 3,5-bis(trifluoromethyl)phenylboronic acid, 2-methoxyphenylboronic acid, 3-methoxyphenylboronic acid, 4-methoxyphenylboronic acid, 2,5-dimethoxyphenylboronic acid, 4,5-dimethoxyphenylboronic acid, 2,4-dimethoxyphenylboronic acid, 2-ethoxyphenylboronic acid, 3-ethoxyphenylboronic acid, 4-ethoxyphenylboronic acid, 4-phenoxyboronic acid, 4-methylenedioxyphenylboronic acid, 2-fluorophenylboronic acid, 3-fluorophenylboronic acid, 4-fluorophenylboronic acid, 2,4-difluorophenylboronic acid, 2,5-difluorophenylboronic acid, 4,5-difluorophenylboronic acid, 3,5-difluorophenylboronic acid, 2-fornylphenylboronic acid, 3-fonnylphenylboronic acid, 4-formylphenylboronic acid, 3-formyl-4-methoxyphenylboronic acid, 2-cyanophenylboronic acid, 3-cyanophenylboronic acid, 4-cyanophenylboronic acid, 3-nitrophenylboronic acid, 3-acetylphenylboronic acid, 4-acetylphenylboronic acid, 3-trifluoroacetylphenylboronic acid, 4-trifluoroacetylphenylboronic acid, 4-methylthiophenylboronic acid, 4-vinylphenylboronic acid, 3-carboxyphenylboronic acid, 4-carboxyphenylboronic acid, 3-aminophenylboronic acid, 2-(N,N-dimethylamino)phenylboronic acid, 3-(N,N-dimethylamino)phenylboronic acid, 4-(N,N-dimethylamino)phenylboronic acid, 2-(N,N-diethylamino)phenylboronic acid, 3-(N,N-diethylamino)phenylboronic acid, 4-(N,N-diethylamino)phenylboronic acid, 2-(N,N-dimethylaminomethyl)phenylboronic acid, furan-2-boronic acid, furan-3-boronic acid, 4-formyl-2-furanboronic acid, dibenzofuran-4-boronic acid, benzofuran-2-boronic acid, thiophene-2-boronic acid, thiophene-3-boronic acid, 5-methylthiophene-2-boronic acid, 5-chlorothiophene-2-boronic acid, 4-methylthiophene-2-boronic acid, 5-methylthiophene-2-boronic acid, 2-acetylthiophene-5-boronic acid, 5-methylthiophene-2-boronic acid, benzothiophene-2-boronic acid, dibenzothiophene-4-boronic acid, pyridine-3-boronic acid, pyridine-4-boronic acid, pyrimidine-5-boronic acid, quinoline-8-boronic acid, isoquinoline-4-boronic acid, 4-benzenebis(boronic acid), phenylboronic acid-pinacol ester, and 4-cyanophenylboronic acid-pinacol ester.

Examples of the base that may be used include, for example, an inorganic base such as a hydroxide, carbonate, hydrogencarbonate, phosphate, carboxylate, or alkoxide of an alkali metal (e.g., sodium, potassium, lithium) or alkaline earth metal (e.g. barium, calcium). The base may be an anhydrous or hydrate form. The base is preferably a hydroxide, carbonate, hydrogencarbonate, phosphate, or carboxylate of the alkali metal or the alkaline earth metal, and more preferably a carbonate or phosphate of the alkali metal or the alkaline earth metal.

Preferred examples of the alkali metal or alkaline earth metal salt include, for example, lithium carbonate, sodium carbonate, potassium carbonate, cesium carbonate, calcium carbonate, barium carbonate, lithium phosphate, sodium phosphate, and potassium phosphate. Sodium carbonate, potassium carbonate or potassium phosphate is more preferred.

The base is usually used in an amount of about 0.1 to 20 moles, preferably 1 to 5 moles, per mol of the boron atom of the boron compound (2). Two or more bases may be used in combination.

The embodiments of the process of the present invention is generally performed using a solvent such as an organic solvent or water or mixtures thereof, preferably in the organic solvent.

Examples of the organic solvent include, for example, an alcohol solvent such as methanol or ethanol; an aprotic polar organic solvent such as N-methylpyrolidone, N,N-dimethylformamide, N,N-dimethylacetamide, dimethylsulfoxide, and acetonitrile; an ether solvent such as diethyl ether, diisopropyl ether, ethylene glycol dimethyl ether, diethylene glycol dimethyl ether, 1,4-dioxane, and tetrahydrofuran; an aromatic hydrocarbon solvent such as benzene, toluene and xylene; and an aliphatic hydrocarbon solvent such as hexane and heptane. One of these solvents may be used alone, or two or more of these solvents may be used in combination. The solvent is used in an amount of generally 1 to 200 times, preferably 5 to 100 times as much as the weight of the organic halide. In particular, the ether or aprotic polar solvent is preferred.

The reaction temperature is generally from 0° C. to 200° C., preferably from 20° C. to 140° C., depending on the structure of the organic halide.

The reaction is preferably performed under an inert gas atmosphere so that deactivation of the catalyst due to oxygen can be prevented. For example, the inert gas may be nitrogen or argon. The reaction may be performed under any pressure (e.g. from pressurized pressure to reduced pressure), but generally under atmospheric pressure.

In the embodiments of the process of the present invention, the organic halide (1), the boron compound (2), the compound of formula (i), and the nickel compound, and the base, and optionally an appropriate solvent are used and may be added in any order. In the process using a reducing agent that can react with the organic halide or the boron compound, the materials should be added in such order that the reducing agent can be prevented from reacting with the halide or the boron compound. For example, such a process may be conducted by adding the organic halide, the boron compound and the base, and optionally an appropriate solvent in any order and then adding, to such a system, a mixture prepared from the nickel compound, the compound of formula (i) and the reducing agent. Alternatively, such a process may be conducted, for example, by preparing a mixture of the nickel compound, the compound of formula (i) and the reducing agent, and then adding to the resulting mixture the organic halide, the boron compound and the base, and optionally an appropriate solvent in optional order. In such a process, a compound comprising the nickel compound and the compound of formula (i) coordinated thereto may be used in place of the mixture of the nickel compound and the compound of formula (i).

After the reaction, the resulting coupling compound can be separated from the reaction mixture typically by adding an aqueous solution of mineral acid such as dilute hydrochloric acid or dilute sulfuric acid to the reaction liquid to acidify it, then typically performing extraction with an organic solvent, washing with water, and removing the solvent by distillation. If desired, the resulting coupling compound may further be purified by any method such as distillation, recrystallization and/or a variety of chromatography.

Examples of the coupling compound (3) include, for example, 1-isopropyl-4-n-nonylbenzene, 2-(2,5-difluorophenyl)butane, 1,6-diphenylhexane, 1-(N,N-dimethylaminophenyl)heptadecafluorooctane, 1-cyclohexyl-2-trifluorophenylbenzene, 12-(4-cyanophenyl)-1-dodecanol, 2-(4-methylenedioxyphenyl)ethyl methyl ether, 6-(9-anthracenyl)-1-hexene, 1-(3-acetylphenyl)-2-methylpropane, 1-(2-ethoxyphenyl)pentane, and 1-(4-methylenedioxyphenyl)butane.

EXAMPLES

The invention is further described in detail by showing the examples below, but such examples are not intended to limit the scope of the invention. Each reaction mixture was analyzed by gas chromatography.

Example 1

In an argon atmosphere, 0.4 mmol (61 mg) of p-methoxyphenylboronic acid, 0.3 nunol (57 mg) of 1-bromooctane, 0.45 mmol (95 mg) of potassium phosphate, 0.015 mmol (2.6 mg) of bis(N-methylimidazole-2-yl)methane, and 0.015 mmol (4.1 mg) of bis(1,5-cyclooctadiene)nickel were mixed with 1 ml of N,N-dimethylacetamide. The resulting mixture was heated to 80° C. and then held at the same temperature for 2 hours under stirring. After the reaction was completed, the reaction mixture was allowed to stand at room temperature. After 10 ml of 1 N hydrochloric acid was added to dissolve potassium phosphate, the reaction mixture was transferred to a separating funnel and extracted with ethyl acetate. The extracted organic layer was washed with a saturated sodium chloride solution. The 4-octylanisole was obtained in a yield of 87% as shown in Table 1.

Examples 2 to 13

The process of Example 1 was repeated in a similar manner except that 0.4 mmol of each of the boron compounds as shown in Table 1 was used in place of p-methoxyphenylboronic acid and 0.30 mmol of each organic halide as shown in Table 1 was used in place of 1-bromooctane and reaction was conducted for the noted period of time in Table 1.

TABLE 1

| Ex. No. | Organic halide compound | Boron compound | Reaction Time | Coupling Product | Yield (%) |
|---|---|---|---|---|---|
| 1 | n-C$_8$H$_{17}$-Br | (HO)$_2$B-C$_6$H$_4$-OCH$_3$ | 2 hr | n-C$_8$H$_{17}$-C$_6$H$_4$-OCH$_3$ | 87 |
| 2 | ↑ | (HO)$_2$B-C$_6$H$_4$-CF$_3$ | ↑ | n-C$_8$H$_{17}$-C$_6$H$_4$-CF$_3$ | 89 |
| 3 | n-C$_8$H$_{17}$-Cl | ↑ | 9 hr | n-C$_8$H$_{17}$-C$_6$H$_4$-CF$_3$ | 80 |
| 4 | ↑ | C$_6$H$_5$-B(OH)$_2$ | ↑ | n-C$_8$H$_{17}$-C$_6$H$_5$ | 85 |
| 5 | ↑ | CH$_3$C(O)-C$_6$H$_4$-B(OH)$_2$ | ↑ | n-C$_8$H$_{17}$-C$_6$H$_4$-C(O)CH$_3$ | 83 |
| 6 | ↑ | (HO)$_2$B-C$_6$H$_4$-OCH$_3$ | ↑ | n-C$_8$H$_{17}$-C$_6$H$_4$-OCH$_3$ | 85 |
| 7 | ↑ | benzofuran-2-yl-B(OH)$_2$ | ↑ | n-C$_8$H$_{17}$-(benzofuran-2-yl) | 74 |
| 8 | n-C$_8$H$_{17}$-Br | ↑ | 2 hr | n-C$_8$H$_{17}$-(benzofuran-2-yl) | 80 |

TABLE 1-continued

| Ex. No. | Organic halide compound | Boron compound | Reaction Time | Coupling Product | Yield (%) |
|---|---|---|---|---|---|
| 9 | HO~~~~~~Cl | ⌬-B(OH)₂ | 9 hr | HO~~~~~~~-Ph | 73 |
| 10 | NC~~~~~Cl | ↑ | ↑ | NC~~~~~~-Ph | 80 |
| 11 | AcO~~~~Cl | ↑ | ↑ | AcO~~~~-Ph | 79 |
| 12 | Cyclohexyl-Br | ↑ | 2 hr | Cyclohexyl-Ph | 80 |
| 13 | sec-alkyl-Br | ↑ | ↑ | sec-alkyl-Ph | 82 |

Examples 14 to 18

The process of Example 1 was repeated in a similar manner except that 0.40 mmol of phenylboronic acid was used in place of p-methoxyphenylboronic acid and that 1 ml of each solvent as in Table 2 was used in place of N,N-dimethylacetamide. The result is shown in Table 2.

TABLE 2

| Ex. No. | Solvent | Reaction Time | Yield (%) |
|---|---|---|---|
| 14 | Tetrahydrofuran | 4 hr | 59 |
| 15 | Ethyleneglycol dimethyl ether | ↑ | 61 |
| 16 | N,N-dimethyl acetamide | 2 hr | 87 |
| 17 | N,N-dimethyl acetamide | 2 hr | 79 |
| 18 | Ethanol | 4 hr | 48 |

Examples 19 to 36

The process of Example 1 is repeated in a similar manner except that 0.40 mmol of boron compound as listed in Table 3 is used in place of p-methoxyphenylboronic acid and that 0.30 mmol of the organic halide compound as shown in Table 3 is used in place of 1-bromooctane, and each solvent as shown in Table 3 is used in place of N,N-dimethylacetamide, thereby the desired compounds as listed in Table 3 are obtained.

TABLE 3

| Ex. No | Organic Halide Compound | Boron compound | Solvent | Coupling Product |
|---|---|---|---|---|
| 19 | (alkyl iodide) | 2-naphthyl-B(OH)₂ | N-methylpyrrolidone | (naphthyl-alkyl) |
| 20 | ↑ | pentenyl-B(OH)₂ | Tetrahydrofuran | (alkenyl-alkyl) |
| 21 | BrCH₂CH₂OCH₂CH₂OEt | 3,4-dimethylphenyl-B(OH)₂ | N,N-dimethylacetamide | (3,4-dimethylphenyl ether) |
| 22 | ↑ | pyridin-3-yl-B(OH)₂ | ↑ | (pyridyl ether) |
| 23 | ↑ | 3-methoxy-5-methylphenyl-B(OH)₂ | Ethyleneglycol dimethyl ether | (methoxy-methylphenyl ether) |
| 24 | (fluorinated alkyl iodide) | 4-(trifluoromethyl)phenyl-B(OH)₂ | ↑ | (fluorinated alkyl-CF₃-phenyl) |
| 25 | ↑ | ↑ | N,N-Dimethylacetamide | ↑ |
| 26 | ↑ | ↑ | Ethanol | ↑ |

TABLE 3-continued

| Ex. No | Organic Halide Compound | Boron compound | Solvent | Coupling Product |
|---|---|---|---|---|
| 27 | cyclohexyl-CH(Pr)-CH2CH2-Br | 2-phenyl-1,3,2-dioxaborinane | Tetrahydrofuran | cyclohexyl-CH(Pr)-CH2CH2-Ph |
| 28 | ↑ | PhB(OH)2 | N-Methylpyrrolidone | ↑ |
| 29 | ↑ | 6,7-dimethyl-2-naphthyl-B(OH)2 | ↑ | cyclohexyl-CH(Pr)-CH2CH2-(6,7-dimethylnaphthalen-2-yl) |
| 30 | 3-oxo-7-chloro-heptan-... with OAc-phenyl chloride | 3-acetoxyphenyl-B(OH)2 | N,N-Dimethylformamide | 3-acetoxyphenyl coupling product with diketone |
| 31 | 3-iodo-4-methylcyclohexan-1-ol | furan-3-yl-B(OH)2 | N,N-Dimethylacetamide | 3-(furan-3-yl)-4-methylcyclohexan-1-ol |
| 32 | ↑ | 4-methoxyphenyl-B(OH)2 | ↑ | 3-(4-methoxyphenyl)-4-methylcyclohexan-1-ol |

TABLE 3-continued
| Ex. No | Organic Halide Compound | Boron compound | Solvent | Coupling Product |
|---|---|---|---|---|
| 33 | 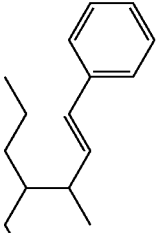 |  | ↑ |  |
| 34 | 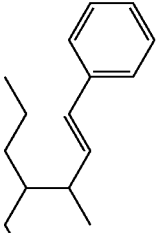 | ↑ | N,N-Dimethylformamide |  |
| 35 | ↑ |  | ↑ | 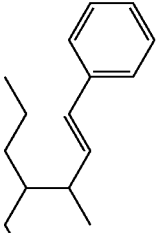 |
| 36 |  | ↑ | N,N-Dimethylacetamide |  |

Example 37

In an argon atmosphere, 0.015 mmol (2.6 mg) of bis(N-methylimidazol-2-yl)methane and 0.015 mmol (4.4 mg) of nickel chloride hexahydrate were mixed with 0.3 ml of ethylene glycol dimethyl ether and stirred at room temperature for 10 minutes to prepare a liquid preparation of the catalyst.

The obtained ethylene glycol dimethyl ether solution was removed from the liquid preparation of catalyst, and the resulting solid material was subjected to infrared absorption spectrum analysis. As a result, a specific peak was observed at 1663 cm$^{-1}$. The liquid preparation of catalyst or the solid material is used in the reaction process under the same conditions as those for Example 1, so that the desired product is obtained.

Comparative Example 1

The process of Example 1 was conducted in a similar manner except that 0.015 mmol (6.5 mg) of 1,4-bis(dicyclohexylphosphino)propane was used in place of bis(N-methylimidazole-2-yl)methane. The recovery rate of unreacted 1-bromooctane was 100%, thus the conversion rate was 0%.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for producing a cross-coupling compound of formula (3):

$$(Y-)_{(n-1)}R^1-R^2-(R^1)_{(n'-1)} \quad (3)$$

wherein R$^1$ represents
a substituted or unsubstituted, linear, branched, or cyclic hydrocarbon group, and
n and n' each represent 1 or 2,
provided that when n and n' are the same, both n and n' are not 2,
R$^2$ represents a substituted or unsubstituted aryl, substituted or unsubstituted heteroaryl or substituted or unsubstituted alkenyl group, and
Y represents R$^2$ or X$^1$, wherein R$^2$ is as defined above, and X$^1$ represents a chlorine, bromine or iodine atom,
which method comprises reacting
an organic halide of formula (1):

wherein R$^1$ is as defined above and carbon atoms at the α and β positions relative to X$^1$ are sp$^3$ carbon atoms, and X$^1$, n and n' are as defined above,
with a boron compound of formula (2):

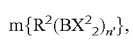

wherein R$^2$ and n' are as defined above,
X$^2$ independently represents a hydroxyl group or an alkoxy or aryloxy group, or X$^2{}_2$ together form an alkylenedioxy or arylenedioxy group, and m represents 1 or 2, and m≦n, and the boron atom is bonded with a sp$^2$ carbon atom of R$^2$ group, or a boronic acid trimer anhydride thereof,
in the presence of a base and a catalyst comprising a nickel compound and a compound of formula (i):

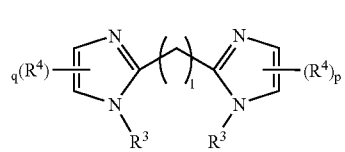

wherein R$^3$ represents a substituted or unsubstituted alkyl group,
R$^4$ represents a hydrogen atom or an substituted or unsubstituted alkyl group,
l represents an integer of 1 to 3, and
p and q independently represent an integer of 0 to 2.

2. The method according to claim 1, wherein R$^3$ is methyl in the compound of formula (i).

3. The method according to claim 1, wherein the boron compound of formula (2) is a compound of formula (4):

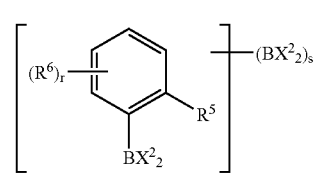

wherein R$^5$ represents a hydrogen atom,
X$^2$ groups independently represent a hydroxyl group or an alkoxyl group, or the alkoxy groups together form an alkylenedioxy group, or
X$^2{}_2$ represent —O—B(R$^{20}$)—O—B(R$^{20}$)—O—, wherein R$^{20}$ represents the phenyl residue as defined in connection with formula (4) above,
r represents an integer of 0 to 4,
s represents 0 or 1, r+s≦4 when the benzene ring does not form a condensed aromatic ring,
R$^6$ groups are the same or different and each independently represent a substituted or unsubstituted aryl group,
a substituted or unsubstituted heteroaryl group, or
a substituted or unsubstituted linear or cyclic alkenyl group, or
R$^6$ groups connected with the adjacent carbon atoms of the benzene ring are bonded to form an ortho-condensed, or ortho and peri-condensed polycyclic aromatic ring.

4. The method according to claim 1, wherein the nickel compound is a nickel salt or a π complex compound of zerovalent or divalent nickel.

5. The method according to claim 1, wherein the nickel compound is selected from the group consisting of nickel chloride, nickel bromide, nickel iodide, nickel nitrate, nickel acetate and bis(1,5-cyclooctadiene)nickel (0).

6. The method according to claim 1, wherein the compound of formula (i) is selected from the group consisting of bis(N-methylimidazole-2-yl)methane, bis(1,2-N-methylimidazole-2-yl)) ethane, and bis(1,3-(N-methylimidazole-2-yl))propane.

7. The method according to claim 2, wherein the boron compound of formula (2) is a compound of formula (4):

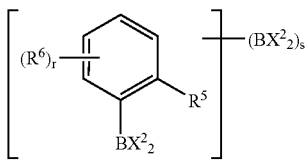 (4)

wherein $R^5$ represents a hydrogen atom, $X^2$ groups independently represent a hydroxyl group or an alkoxyl group, or the alkoxy groups together form an alkylenedioxy group, or $X^2{}_2$ represent —O—B($R^{20}$)—O—B($R^{20}$)—O—, wherein $R^{20}$ represents the phenyl residue as defined in connection with formula (4) above, r represents an integer of 0 to 4, s represents 0 or 1, r+s≦4 when the benzene ring does not form a condensed aromatic ring, $R^6$ groups are the same or different and each independently represent a substituted or unsubstituted aryl group, a substituted or unsubstituted heteroaryl group, or a substituted or unsubstituted linear or cyclic alkenyl group, or $R^6$ groups connected with the adjacent carbon atoms of the benzene ring are bonded to form an ortho-condensed, or ortho and peri-condensed polycyclic aromatic ring.

8. The method according to claim 2, wherein the nickel compound is a nickel salt or a π complex compound of zerovalent or divalent nickel.

9. The method according to claim 3, wherein the nickel compound is a nickel salt or a π complex compound of zerovalent or divalent nickel.

10. The method according to claim 7, wherein the nickel compound is a nickel salt or a π complex compound of zerovalent or divalent nickel.

11. The method according to claim 7, wherein the nickel compound is selected from the group consisting of nickel chloride, nickel bromide, nickel iodide, nickel nitrate, nickel acetate and bis(1,5-cyclooctadiene)nickel (0).

12. The method according to claim 7, wherein the compound of formula (i) is selected from the group consisting of bis(N-methylimidazole-2-yl)methane, bis(1,2-N-methylimidazole-2-yl)) ethane, and bis(1,3-(N-methylimidazole-2-yl)) propane.

* * * * *